US00PP08779P

United States Patent [19]

Pittman

[11] Patent Number: Plant 8,779

[45] Date of Patent: Jun. 14, 1994

[54] *ILEX VOMITORIA* VARIETY NAMED 'CONDEAUX'

[75] Inventor: Jerry B. Pittman, Mobile, Ala.

[73] Assignee: Flowerwood Nursery Inc., Mobile, Ala.

[21] Appl. No.: 100,387

[22] Filed: Aug. 2, 1993

[51] Int. Cl.[5] ..... A01H 5/00

[52] U.S. Cl. ..... Plt./65

[58] Field of Search ..... Plt. 65

*Primary Examiner*—James R. Feyrer

[57] ABSTRACT

The new plant is readily distinguishable from other *Ilex vomtoria* as the Ilex described herein does not have the same characteristics as other Ilex in growth habit, or foliage color as described in horticultural literature.

2 Drawing Sheets

BACKGROUND OF THE INVENTION

This new variety of *Ilex vomitoria* was found as a sport of *Ilex vomitoria* 'Stokes Dwarf' maintained in the Flowerwood Nursery at Dauphin Island Parkway, Mobile, Ala. The sport was found in September, 1988. The new and distinct *Ilex vomitoria* plant of this invention comprises a novel and valuable holly plant of dense, compact and attractive mounding habit. This plant is a color sport of 'Stokes Dwarf' and exhibits all of ther outstanding attributes of the parent plant but differs primarily from and attractively contrasts with the parent plant in color of new growth. The new growth of this plant is interestingly and clearly red due to anthocyanin, which is of distictly higher concentration than in the parent variety. As with the parent plant, the plant of this invention, which has been named 'Condeaux', may be advantageously employed as a specimen appointment, a ground cover, in either formal or informal groupings, and is quite attractive in mass plantings. The plant serves equally well in foundation plantings or as a single specimen and is adapted for culture as a potted plant. This plant is responsive to pruning and training and may be employed in forming dense, attractive hedges, and maintained without an excessive amount of care. This plant is easy to care for and maintain in size due to its small stature, heavy branching and dense canopy. It is highly drought tolerant, insect and disease tolerant and balanced in growth, and is well adapted to culture in most of the Sunbelt States. Having short internodes, this plant has a natural propensity to remain small and is thereby a valuable contribution to the industry for landscape uses which require a plant which can be maintained in a small size to maturity, so as not to outgrow its intended mature dimensions in home gardens which tend to be smaller by trend.

The low mounding habit of this plant is similar to *Ilex cornuta* 'Rotunda', however, it doesn't have the dangerous spines which can be a problem when young children are around. This plant can be used in place of *Ilex crenata* varieties to produce a more colorful landscape which requires less pruning.

Asexual propagation of the new plant by cuttings has been under Mr. Pittman's direction at the same location. The increased number of plants were evaluated and demonstrated stability of the new characteristics from generation to generation.

SUMMARY OF THE INVENTION

The following are the most outstanding and distinguishing characteristics of this new cultivar when grown under normal horticultural practices in Mobile, Ala.

1. Dense and mounding in nature.
2. The Reddish/Purple color of the foliage is unique and offers a novel and strikingly appealing contrast of new foliage to old foliage in plants of this market class.
3. Hardy to zone 7.
4. Heat and drought tolerant.
5. Will tolerate excess water better than Japanese hollies.
6. Relatively pest resistant.
7. Very desirable in planters.
8. Good ground cover.

DESCRIPTION OF THE DRAWINGS

This new variety of *Ilex vomitoria* is illustrated by the accompanying photographic prints in which.

Figure 1:
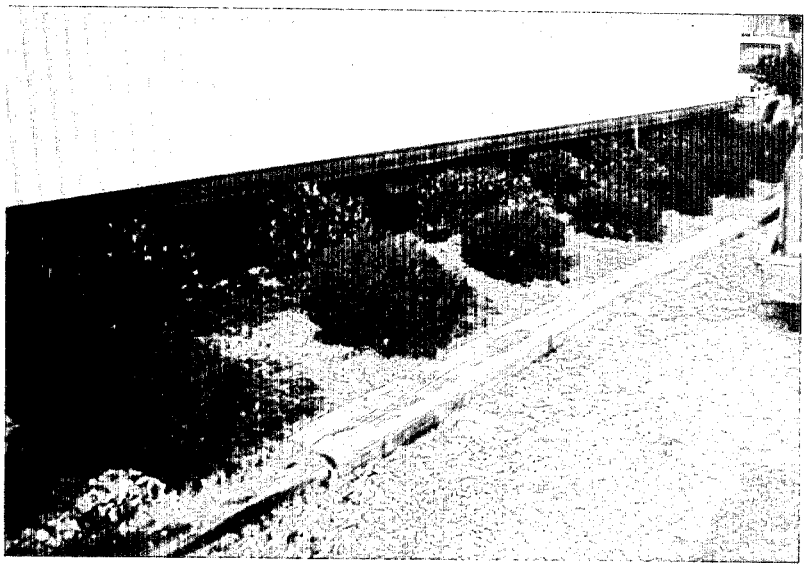
FIG. 1 discloses the low growing, dense and oval nature of the new variety. It also shows the effective use and nature of use of the new variety in an established landscape planting.
Figure 2:
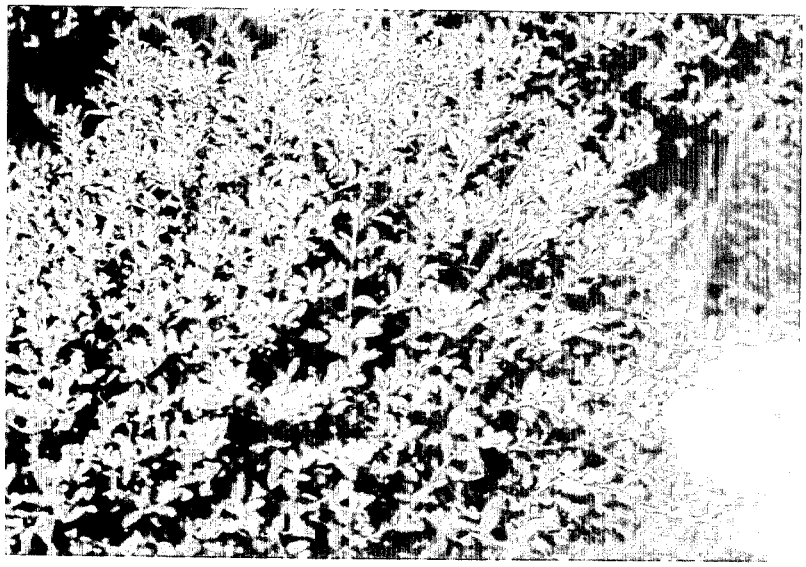
FIG. 2 discloses the unusual reddish/purple pigmentation of the leaves, petioles, and stems of the juvenile growth.
Figure 3:
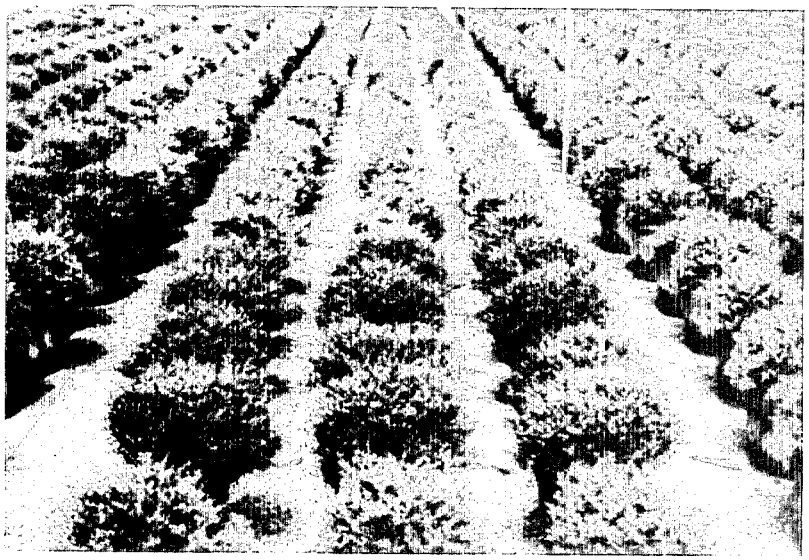
FIG. 3 shows twelve of the new variety of Ilex along with many of the parent variety 'Stokes Dwarf'. The reddish/purple color is quite evident in the new variety.
Figure 4:
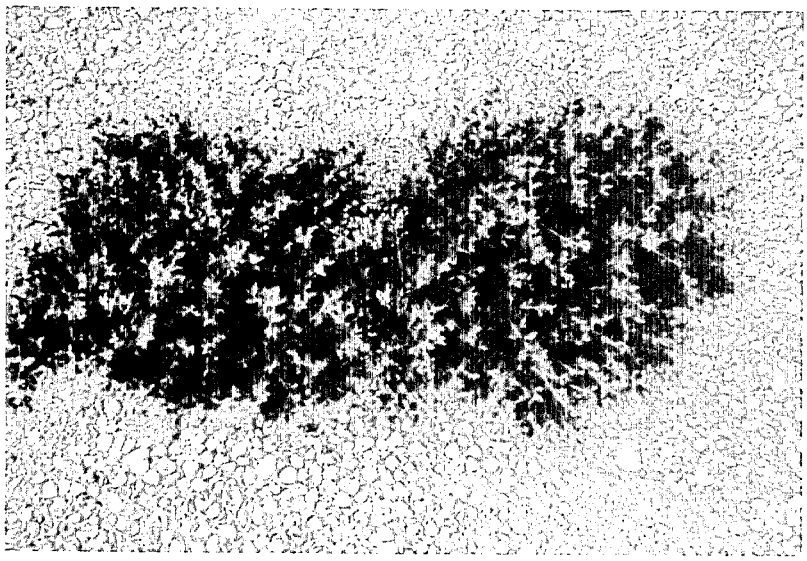
FIG. 4 is a side-by-side photograph with the parent variety 'Stokes Dwarf' which shows the reddish/purple coloration of the new variety.

The colors shown are photographically as nearly true as is reasonably possible to obtain by conventional photographic procedures. The colors of the various plant parts are defined with reference to The Royal Horticultural Society Colour Chart. Description of colors in ordinary terms are presented where appropriate for clarity in meaning.

BOTANICAL DESCRIPTION OF THE PLANT

The following is a detailed description of the new variety of *Ilex vomitoria* based on my observations made of plants grown in wholesale commercial production practices, in greenhouses, and established landscape plantings in Mobile, Ala.

Distinctive Characteristics

| Characteristics | 'Condeaux' | 'Stokes Dwarf' | 'Nana' |
|---|---|---|---|
| Height (Mature) | 120–150 cm | 120–150 cm | 150–180 cm |
| Width (Mature) | 300–330 cm | 300–330 cm | 330–360 cm |
| Leaf Length | 2 cm | 2 cm | 2.5 cm |
| Leaf Width | 1 cm | 1 cm | 1.5 cm |
| Stem | purple | light purple | light purple |
| Flower | white | white | white |
| Foliage (New) | greyed-purple | red-purple | red-purple |
| Fruit | none | none | red |

The plant from which all above varieties originated has the botanical name Aquifoliaceae *Ilex vomitoria.*

*Ilex vomitoria* 'Nana' was named by Mr. Tom Dodd in 1940. It has a slightly larger growth habit and leaf size. It is female and produces red berries. I visited Mr. Tom Dodd at Tom Dodd Nursery in Semmes, Ala. on Jul. 8, 1993 and we inspected his stock plants which were planted in 1960.

*Ilex vomitoria* 'Stokes Dwarf' was found by Mr. Sam Stokes and registered in 1961 by Professor Sigmond Solymosy of Southwestern Louisiana University with the American Holly Society. It is a male and produces no fruit. It is from this variety, *Ilex vomitoria* 'Stokes Dwarf', that I found the new plant, *Ilex vomitoria* 'Condeaux'. This new variety will be sold under the trademark name Bordeaux. It will be listed *Ilex vomitoria* Bordeaux TM 'Condeaux'.

Classification:

*Botanic.—Ilex vomitoria* 'Condeaux'.

Form: Dense oval shape.

Texture: Fine.

Height: 4–5 feet.

Width: 5–6 feet.

Growth: Low growing, dense and oval. Slow to moderate growth rate.

Leaves: Alternate, simple, evergreen, oval to elliptic, tapered base, blunt at apex, and vary in size from ½ inch to 1 inch long. The surface texture of the leaf is glossy and glabrous. The bottom surface, matte and glabrous. The texture contrast between the top and bottom leaf surfaces are indentical to the parent plant. The margin of the leaf is shallowly toothed usually to the base which is the same as the parent but separates it from *Ilex crenata.* Leaves are nearly always flat and the petiole is ⅛" long. The midribs are slightly raised top and bottom, however, the veins are not. The mature leaves of this plant differ from the parent plant in that they are darker green in color. The mature leaf of the parent plant is Yellow-Green Group 146 A while the leaf of the new plant is Yellow-Green Group 147 A. The underside of both are identical Green Group 138 B.

In 1991, the date of initial spring growth was March 14, in Mobile, Ala. There was a second flush of growth June 25 and a final flush of growth that Fall ending October 12, also in Mobile, Ala. This growth pattern was indentical to the parent plant. The internodes length of this plant and the parent plant is about 0.5 cm when grown in full sun and 0.5 cm to 1.0 cm when grown in the shade. As would be expected either plant grown in shade results in a taller less dense plant with larger leaves.

The average length of terminal growth of the initial spring flush is about 7.5 cm for a plant in full sun and about 10.5 cm when grown in shade. After this initial flush we normally trim the plant lightly and there is another flush of about 5.5 cm which occurs in early to mid summer, we then trim the second and final time in early fall before the final flush of growth which measures about 6.5 cm. We finish in the fall with a one gallon plant about 24 cm tall and 28 cm wide. I have not noticed a difference in vigor between this plant and the parent.

Although there are many variables involved it should take about 10–12 years for this plant to reach mature height of 3–4 feet tall and width 4–5 feet. A 25 year old plant may be 5 feet high and 8–10 feet wide. In the landscape little or no pruning is necessary to produce a full mounding shrub in full sun. In shade, however, some trimming may be needed to produce the same effect.

Stems: Have a pronounced purple pigmentation on the young shoots. Generally a light gray after one or more years. Stems are puberulent. The plant is densely branched throughout the entire shrub.

Flowers: Small creamy white, inconspicuous from March–May. Flower structure of this plant is identical to those of the parent plant. *Ilex vomitoria* is a dioecious plant. *Ilex vomitoria* 'Stokes Dwarf' is a male plant and since *Ilex vomitoria* 'Condeaux' is a sport off of *Ilex vomitoria* 'Stokes Dwarf' is too is a male plant. The flowers are staminate, clustered in the leaf axils, and 4-merous. Petals united at base, imbricate in bud. Anthers are yellow (Yellow Group 11C) and open lengthwise. Pistil is not developed. The flowers are 2–5 mm long and 2–5 mm wide. There is no fragrance and a plant 12" tall and 12" wide will have several hundred flowers producing a moderate amount of functional pollen. In 1991 the blooming period began March 25, in Mobile, Ala. and ended May 12. The blooming period is basically indentical to *Ilex vomitoria* and *Ilex vomitoria* 'Stokes Dwarf'. Since this plant is male it will not result in the occurrence of unwanted seedlings or bird visitations.

Fruit: None.

Color: The colors are described according to the nearest colors of The Royal Horticultural Society Colour Chart. The terminal growth consisting of 3 cm of stem and from 6–8 leaves is a deep purple color (greyed-purple 137A).

The terminal stem growth 4 cm back is also purple (red- purple group 59D). The immature stem from 4 cm to the old wood is a light green (yellow-green group 148C), and the old wood is gray (greyed-green group 194A).

Culture: Grows well in a wide range of conditions, tolerates sun to part shade. Grows in nearly any soil type, from moist to very dry and sand to clay. Responds well to mulching and light applications of fertilizer. Very little pruning is needed. Can be sheared. Propagated with semi-hardwood cutting in the fall.

Pest: Leaf minor can be a problem. This plant is resistant to the nematode injury which plagues the Japanese Hollies in sandy soil.

I claim:

1. A new and unique variety of *Ilex vomitoria* named *Ilex vomitoria* 'Condeaux' as herein shown and described, is characterized by its very low growth habit and unique juvenile foliage coloration, the dense, compact, mounding growth habit will fill numerous landscape needs for ground covering, groupings and mass plantings, foundation plantings, unusual foliage coloration, drought tolerance, requiring less maintenance, and freedom from disease and insects with a wide soil tolerance.

* * * * *